(12) United States Patent
Krasnow (10) Patent No.: US 11,267,793 B1
(45) Date of Patent: *Mar. 8, 2022

(54) ADAPTIVE OPTICAL PATH WITH VARIABLE FOCAL LENGTH

(71) Applicant: Valve Corporation, Bellevue, WA (US)

(72) Inventor: Benjamin David Krasnow, Redwood City, CA (US)

(73) Assignee: Valve Corporation, Bellevue, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/595,268

(22) Filed: Oct. 7, 2019

Related U.S. Application Data

(63) Continuation of application No. 13/669,668, filed on Nov. 6, 2012, now Pat. No. 10,442,774.

(51) Int. Cl.
*C07D 241/26* (2006.01)
*G02B 26/06* (2006.01)
(Continued)

(52) U.S. Cl.
CPC ......... *C07D 241/26* (2013.01); *G02B 26/001* (2013.01); *G02B 26/06* (2013.01); *G02B 26/0833* (2013.01)

(58) Field of Classification Search
CPC .... G02F 1/167; G02F 1/0102; G02F 1/13306; G02F 1/0128; G02F 1/0136; G02F 1/1313; G02F 1/1334; G02F 1/19; G02F 1/21; G02F 1/0131; G02F 1/0147; G02F 1/13318; G02F 1/133514; G02F 1/1339; G02F 1/1347; G02F 1/155; G02F 1/163; G02F 1/1681; G02F 1/172; G02F 1/225; G02B 26/005; G02B 26/06; G02B 26/02; G02B 26/0833; G02B 27/0927; G02B 26/08;
(Continued)

(56) References Cited

U.S. PATENT DOCUMENTS

7,639,208 B1 * 12/2009 Ha ..................... G02B 27/0172
345/204
2004/0051846 A1 3/2004 Blum et al.
(Continued)

*Primary Examiner* — William R Alexander
*Assistant Examiner* — Sharrief I Broome
(74) *Attorney, Agent, or Firm* — Seed Intellectual Property Law Group LLP (57) ABSTRACT

Methods and systems are disclosed relating to a lens system that allows for simultaneous focus of near and far-away images with one pair of glasses, heads-up-displays (HUDs), and the like, without the need to move the user's eyes. This lens system may be used in a HUD application, for example, where the user may focus on a display lens that may be approximately one inch from the eye to view computer-generated information such as altitude, temperature, directions, and the like, and simultaneously view the individual's surroundings. The lens system may include a liquid lens that when modulated may vary from a near-focus state to a far-focus state rapidly by using an electrowetting or piezoelectric hydraulic actuator. This variable rate lens may be multiplexed at a rate that allows both near and far-away images to appear in focus simultaneously through the advantageous use of a user's persistence of vision.

16 Claims, 9 Drawing Sheets

(51) Int. Cl.
*G02B 26/08* (2006.01)
*G02B 26/00* (2006.01)

(58) Field of Classification Search
CPC ........ G02B 2027/0118; G02B 21/0076; G02B 26/007; G02B 26/023; G02B 27/0068; G02B 27/0988; G02B 27/283; G02B 27/286; G02B 27/58; G02B 21/0032; G02B 21/0068; G02B 21/0092; G02B 21/06; G02B 21/10; G09G 2320/066; G09G 5/10; G09G 2320/0626; G09G 2320/064; G09G 2320/0646; G09G 2320/0666; G09G 2320/0693; G09G 2330/021; G09G 2358/00; G09G 2360/145; G09G 2380/12; G09G 3/001; G09G 3/02; G09G 3/34; G09G 3/3413; G09G 3/3426; G09G 3/344; G09G 3/346; G09G 3/38; G09G 5/00; H01S 3/0057; H01S 3/0085; H01S 5/0085; H01S 2301/02; H01S 2301/03; H01S 2301/08; H01S 3/005; H01S 3/0064; H01S 3/0071; H01S 3/0092; H01S 3/025; H01S 3/0405; H01S 3/042; H01S 3/08013; H01S 3/08059; H01S 3/08086; H01S 3/083; H01S 3/10015; H01S 3/10053; H01S 3/10092; H04N 9/3155; H04N 13/341; H04N 2013/403; H04N 2213/008; H04N 5/2254; H04N 5/58; H04N 9/3126; H04N 9/3161; H04N 9/3194; H04N 9/3197; H04N 13/243; H04N 13/25; H04N 13/254; H04N 13/302; H04N 13/383; H04N 13/39; H04N 13/398; H04N 17/002; H04N 2209/047; H04N 5/2253; B32B 17/10761; B32B 2551/00; B32B 17/00; B32B 17/10036; B32B 17/10155; B32B 17/10302; B32B 17/10486; B32B 17/10495; B32B 17/10504; B32B 17/10513; B32B 17/10532; B32B 17/10633; B32B 2307/202; B32B 2307/402; B32B 2307/42; B32B 2307/422; B32B 2310/0843; B32B 2315/08; B32B 2419/00; B32B 2605/006; G01J 3/0224; G01J 3/0297; G01J 4/00; G01J 4/04; G01J 11/00; G01J 1/0228; G01J 1/0295; G01J 1/0425; G01J 1/0444; G01J 1/0492; G01J 1/20; G01J 1/22; G01J 1/28; G01J 1/42; G01J 1/4228; G01J 1/4257; G01J 1/46; G01J 2003/1213; G01J 2003/452; G01J 3/00
See application file for complete search history.

(56) References Cited

U.S. PATENT DOCUMENTS

| | | | |
|---|---|---|---|
| 2006/0018651 A1* | 1/2006 | Cho | G03B 13/00 396/111 |
| 2006/0067663 A1 | 3/2006 | Kita | |
| 2007/0052876 A1 | 3/2007 | Kaufman et al. | |
| 2007/0194630 A1* | 8/2007 | Mignard | G02B 26/001 310/10 |
| 2008/0159586 A1* | 7/2008 | Van Leest | G06T 1/0085 382/100 |
| 2011/0038057 A1* | 2/2011 | Dharmatilleke | G02B 3/14 359/694 |
| 2011/0075257 A1 | 3/2011 | Hua et al. | |
| 2011/0085050 A1* | 4/2011 | Dowski, Jr | H04N 5/23212 348/222.1 |
| 2012/0235900 A1* | 9/2012 | Border | G06F 3/011 345/156 |

* cited by examiner

| Contact angle | Degree of wetting | Strength of: Solid/liquid interactions |
|---|---|---|
| θ = 0 | Perfect wetting | strong |
| 0 < θ < 90° | high wettability | strong weak |
| 90° ≤ θ < 180° | low wettability | weak |
| θ = 180° | perfectly non-wetting | weak |

ADAPTIVE OPTICAL PATH WITH VARIABLE FOCAL LENGTH

BACKGROUND OF THE DISCLOSURE

1. Field of the Disclosure

The disclosure relates generally to methods and systems for variable focus lens, and, more specifically according to aspects of certain embodiments, to methods and systems for providing variable focus lenses for use, for example, with heads-up displays for augmented reality applications and for use within glasses for applications for improving eyesight.

2. General Background

Glasses, also known as eyeglasses, spectacles or simply specs are frames bearing lenses worn in front of the eyes. They are normally used for vision correction and are worn by many individuals. Some individuals may see near objects well, while others may see far objects well. Some individuals may not see either well. There are several solutions for correcting these issues today.

For those that have one issue, there are single lenses that correct for either nearsighted or farsighted issues. But as people age, their ability to focus is lessened and many decide to use multiple-focus lenses, which may be bifocal or even trifocal, to cover all the situations in which they use their sight. Traditional multifocal lenses have two or three distinct horizontal viewing areas, each requiring a conscious effort of refocusing. Some modern multifocal lenses, such as progressive lenses (known as no-line bifocals), give a smooth transition between these different focal points, unnoticeable by most wearers of glasses, while other glasses have lenses specifically intended for use with computer monitors at a fixed distance. Individuals may have several pairs of glasses, one for each task or distance, with specific glasses for reading, computer use, television watching, and writing.

Corrective lenses are used to correct refractive errors of the eye by modifying the effective focal length of the lens in order to alleviate the effects of conditions such as nearsightedness (myopia), farsightedness (hyperopia), astigmatism, or presbyopia.

Figure 1:
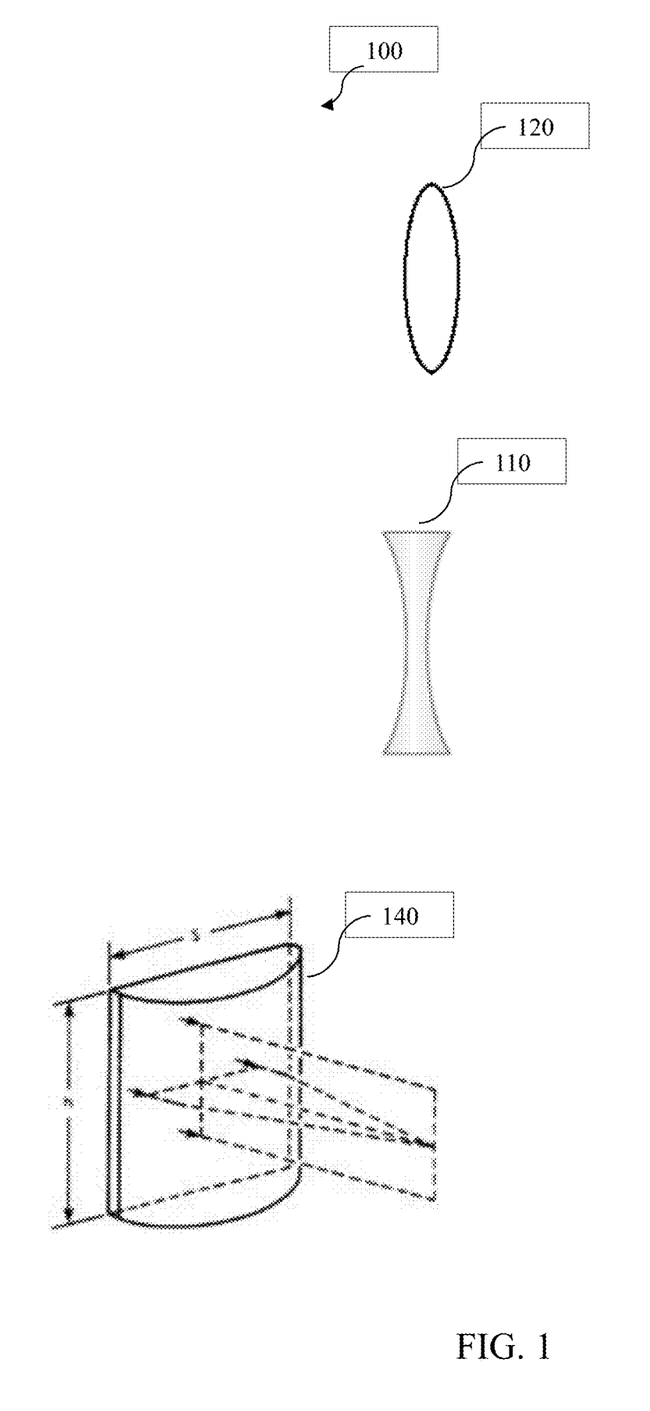
FIG. 1 depicts lenses with convex, concave and cylindrical shapes.
Figure 2:
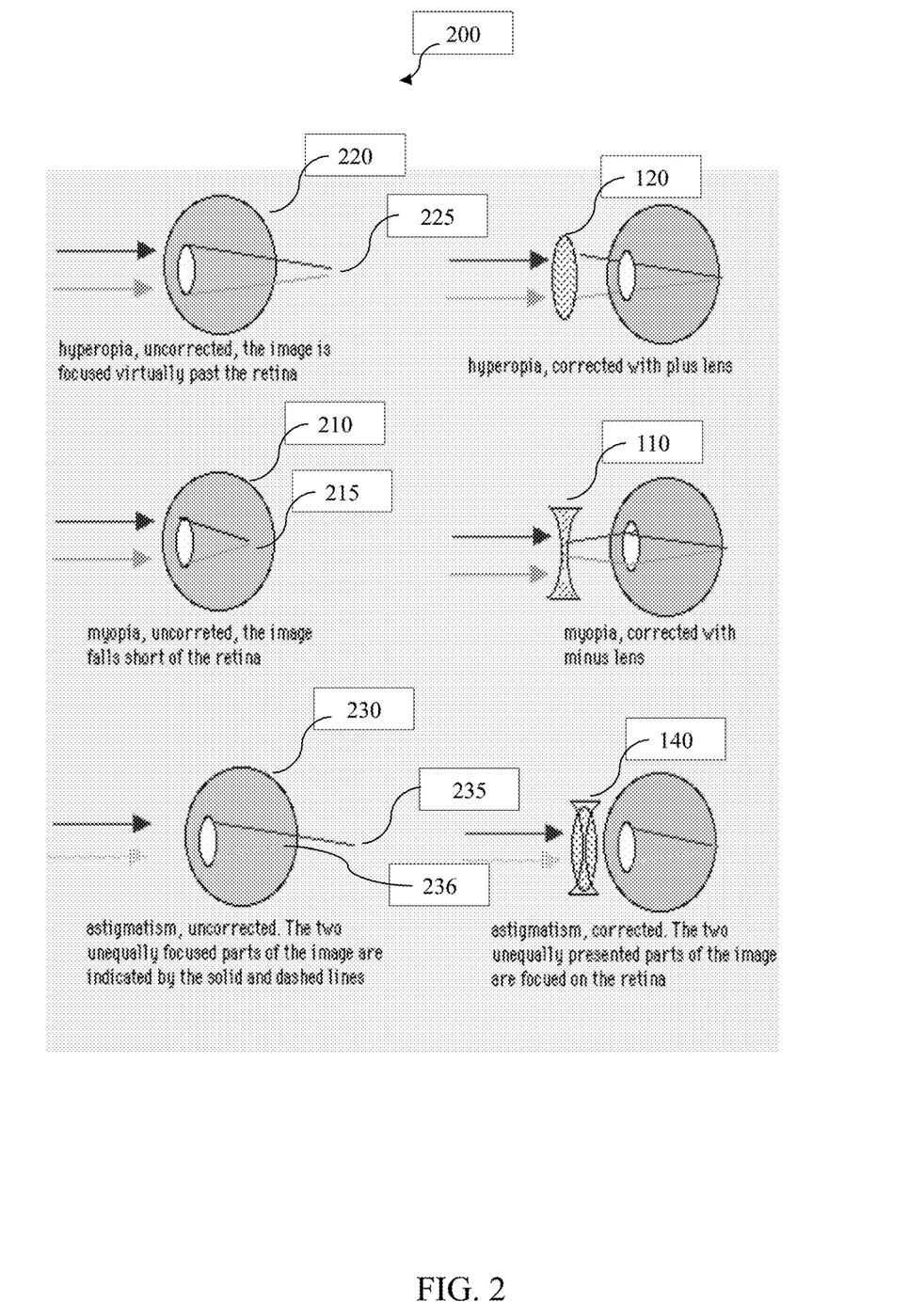
FIG. 2 depicts a set of different common eye focusing issues and the lens corrections that are applied to the eye to address each issue.

These four types of vision deficiencies and their typical methods of correction are explained here (with reference to FIGS. 1 and 2 and the reference numerals that are used in those figures):

First, myopia 210 is a vision disorder that causes far objects to appear blurred but near objects are seen clearly. Individuals suffering from myopia are prescribed eyeglasses with concave lenses 110, which compensate for the refraction error by moving the image of the distant objects that may not be seen clearly backward 215 onto the retina.

Second, correcting hyperopia 220 is normally done with eyeglasses with convex lenses. With this disorder, the patients may see distant objects clearly but they have trouble with seeing objects that are close to them. Eyeglasses with convex lenses 120 compensate for the refraction errors by moving the image of a distant object forward 225 onto the retina.

Third, astigmatism 230 is typically corrected with a cylindrical lens 140. This disorder is caused by a non-uniform curvature in the refractive surfaces of the eye, which leads to an abnormality in focusing the light rays on the retina. As a result, a part of the light rays 236 are focused on the retina and the other part are focused behind 235 it or in front of it. Astigmatism correcting lens is a cylindrical type lens 140 and therefore bends light in only that direction.

Fourth, presbyopia is a condition where the eye exhibits a progressively diminished ability to focus on near objects with age, which is caused by the eye's crystalline lens losing elasticity. It is more frequent in people over 40 years old and it is corrected with convex lenses 120. These patients need reading or bifocal eyeglasses.

The primary disadvantage of all of these types of glasses is that they typically do not allow the individual wearing them to simultaneously focus on near and far objects without moving their eyes or in some cases changing their glasses entirely. They all typically require an individual to focus on near objects by viewing through one of the segments of the lens or focus on far objects by viewing through another portion of the lens. This does not work when using a Heads up Display (HUD) where focusing on a display lens that is approximately 1 inch from the eye to view computer-generated information such as compass reading, altitude, temperature, etc. and simultaneously viewing the individuals surrounding that are further away is required.

Figure 3:
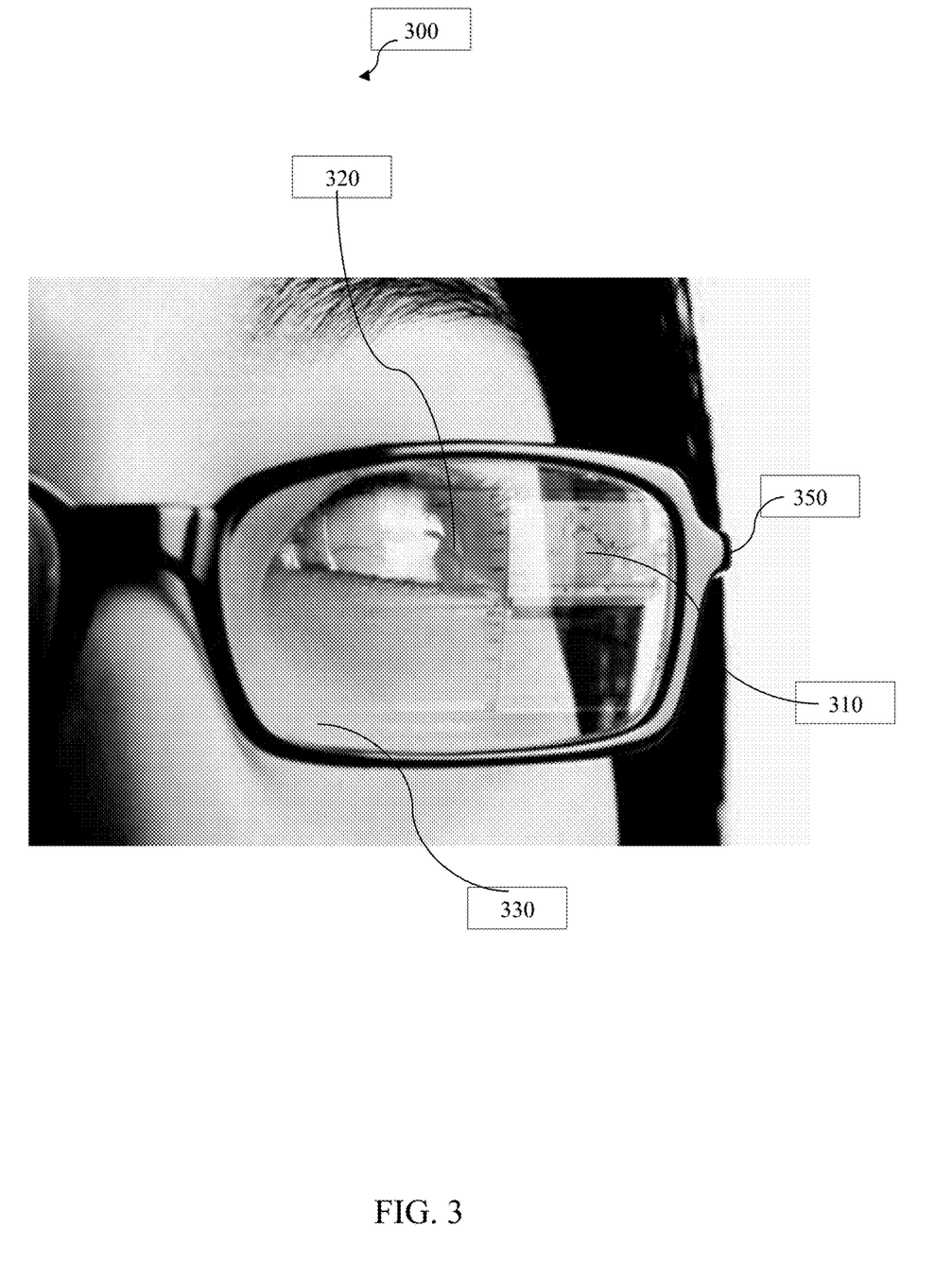
FIG. 3 depicts a high-level overview of a heads up display (HUD) system.

FIG. 3 illustrates the drawbacks of the prior art. The HUD glasses shown have a computer generated image 310 displayed on the lens 330 of the glasses 350. The computer generated image is displayed approximately 1 inch from the eye 320. It is seen that the eye 320 may need to move to focus on one segment of the computer-generated information (near-focus objects) or the eye 320 may need to move to another location to focus on the objects in the individual's actual surroundings (far-focus objects). Accordingly, it is desirable to address the limitations in the art. For example, there exists a need to provide for systems and methods that may improve lenses relatively to allow simultaneous viewing of near-focus and far-focus objects for HUD applications as well as many others.

BRIEF DESCRIPTION OF THE DRAWINGS

By way of example, reference will now be made to the accompanying drawings, which are not to scale.

DETAILED DESCRIPTION

Those of ordinary skill in the art will realize that the following description of the present invention is illustrative only and not in any way limiting. Other embodiments of the invention will readily suggest themselves to such skilled persons, having the benefit of this disclosure. Reference will now be made in detail to specific implementations of the present invention as illustrated in the accompanying drawings. The same reference numbers will be used throughout the drawings and the following description to refer to the same or like parts.

In certain embodiments, methods and systems relating to providing a mechanism that allows for simultaneous viewing of near-focus and far-focus objects through the use of variable focal length lenses are described. Aspects of this invention may allow for the capability to rapidly and dynamically adjust the far focal length and the near focal length allowing for reading a display lens that is approximately one inch away (near-focus) from the eye and seeing the actual surroundings (far-focus) simultaneously.

Certain embodiments relate to a lens system that allows for substantially simultaneous focus of near and far-away images while gazing through a lens system, comprising a variable focus lens, and a modulation device connected to the variable focus lens for modulating the focus of the variable focus lens to enable substantially simultaneous focus of near and far-away images while gazing through the lens system. The variable focus lens may be a liquid lens. A voltage supply may be connected to the variable focus lens, wherein the modulation device varies the focus of the variable focus lens by varying the voltage supplied to the variable focus lens. Alternatively, a current supply may be connected to the variable focus lens, wherein the modulation device varies the focus of the variable focus lens by varying the current supplied to the variable focus lens. The modulation device may be configured to modulate the focus of the variable focus lens between at least one near image and at least one far-away image to enable substantially simultaneous viewing of the at least one near image and the at least one far-away image. The modulation device may be a multiplexer. The multiplexer may be configured to multiplex the focus of the variable focus lens between at least one near image and at least one far-away image to enable substantially simultaneous viewing of the at least one near image and the at least one far-away image.

Certain embodiments include an electro wetting device or a piezoelectric hydraulic actuator for varying the focus of the variable focus lens in response to an input from the modulation device.

In lens systems according to certain embodiments the modulation device changes the variable focus lens from a convex lens to a concave lens. In other embodiments, the variable focus lens changes the lens from a first convex lens to a second convex lens, from a first concave lens to a second concave lens, or from a concave lens to a convex lens.

Certain embodiments include a lens system that allows for simultaneous focus of near and far-away images while gazing through a lens system, comprising an occluding lens system comprising a variable focus lens and an occluding element, and a modulation device connected to an input of said occluding lens system, said modulation device modulating said input to the occluding lens system for controlling at least one focus image. The input may be a voltage supply or a current supply. The modulation device may be configured to modulate the focus of the variable focus lens between at least one near image and at least one far-away image to enable substantially simultaneous viewing of the at least one near image and the at least one far-away image. The modulation device may be a multiplexer, and may be configured to multiplex the focus of the variable focus lens between at least one near image and at least one far-away image to enable substantially simultaneous viewing of the at least one near image and the at least one far-away image. The occluding lens system modulates a blocking device on the outward facing surface of the variable focus lens.

Certain other embodiments include a lens system that allows for simultaneous focus of near and far-away images, comprising a variable focus lens, an occluding element for selectively blocking at least a portion of the field of view of the variable focus lens to prevent viewing of far-away images through the variable focus lens, and a modulation device connected to the variable focus lens for modulating the focus of the variable focus lens. The occluding element may block at least a portion of the field of view of the variable focus lens while the focus state of the variable focus lens is being changed.

Other embodiments include a method for focusing on near and far-away images while gazing through a lens system, comprising the steps of providing a variable focus lens, and modulating an input to the variable focus lens to vary the focus of the variable focus lens to enable substantially simultaneous focus of near and far-away images while gazing through the lens system. The variable focus lens may be a liquid lens. The input may comprise a voltage or a current. The modulating step may comprise modulating the focus of the variable focus lens between at least one near image and at least one far-away image to enable substantially simultaneous viewing of the at least one near image and the at least one far-away image, and may be performed by a multiplexer. The modulating step may comprise modulating the focus of the variable focus lens between at least one near image and at least one far-away image to enable substantially simultaneous viewing of the at least one near image and the at least one far-away image. The input may be provided to an electro wetting device or to a piezoelectric hydraulic actuator to vary the focus of the variable focus lens. The method may involve changing the variable focus lens from a convex lens to a concave lens, from a first convex lens to a second convex lens, from a first concave lens to a second concave lens, from a concave lens to a convex lens, or from a first convex lens to a second convex lens to a first concave lens to a second concave lens.

In certain embodiments, an adaptive optical path element such as a liquid lens, switchable diffracting grating, electroactive polymers, etc. may be placed between the transparent display or lens 330 and the user's eyes 320. Taking a liquid lens as an example, a variable-focus lens may generate either a convex or a concave lens when a voltage is applied. The liquid lens may also generate a convex lens and a more convex lens, or a concave lens and a more concave lens or any other combination of lenses. This may occur because the liquid within the lens forms a different focal length when different voltages are applied to the liquid lens assembly. The process may be performed by actuating a liquid lens by using electro wetting or using a piezoelectric hydraulic actuator to change the properties to focus on far objects, such as focusing on the surroundings or to change the properties to focus on the near objects, such as the computer generated display that may be within approximately one inch of an eye.

An alternate form of this invention may use an optical path occluding (blocking) technology on the outward facing (furthest from the eye) surface of the display lens. The occluding technology may work by not blanking the display lens during the far-focus state so as to see through the display lens as one may look through a piece of glass, and during the near-focus state, blocking the outside world so the eye 320 may focus on the image 310 on the display or lens 330 that may be approximately one inch away from the eye.

In certain embodiments, a variable focus lens such as a liquid lens may be used with an optical path occluding technology on the outward facing (furthest from the eye) surface of the display lens. The occluding device may block the optical path when the variable focus lens is changing states such as from convex to concave states and not blocking the optical path when it is at steady-state. Steady-state may occur when the variable focus lens is not varying, sometimes referred to the dwell time or dwell state.

Certain embodiments may apply the addition of multiplexing to these variable optical path elements to allow the user to view both the near and far away objects simultaneously. For a liquid lens, multiplexing the focus length states of the lens between near and far focus states at a certain rate may allow for both of these states to be viewed simultaneously. In certain embodiments, by performing this with a switching time of approximately 1 ms and a steady-state time (dwell time) of typically 8 ms between focal length switches, both the outside world and the image on the display lens that may be approximately one inch from the eye may appear in focus at all times.

Certain embodiments may apply the addition of multiplexing while using occluding technology. Multiplexing the occluding object to block the optical path or not block the optical path at a certain rate may allow for near and far focus states to be viewed simultaneously. By performing this with a switching time of approximately 1 ms and a steady-state time (dwell time) of typically 8 ms between the occluding state and the non-occluding state, both the outside world and the image on the display lens that may be approximately one inch from the eye may appear in focus at all times. The occluding state may be where the occluding object is blocking the optical path in full or partially and the non-occluding state may be where the occluding object is blocking the optical path in full or partially.

In certain embodiments, the optical path may use variable focus lenses, occluding technology, and multiplexing to create an optical near and far state. This may be accomplished by using an occluding object to block the optical path while the variable focus lens is changing state and by removing the occluding object when the lens is at steady-state (not varying focus state). In certain embodiments, by performing this with a switching time of approximately 1 ms and a steady-state time (dwell time) of typically 8 ms between the occluding state and the non-occluding state, both the outside world and the image on the display lens may appear in focus at all times.

Figure 4:
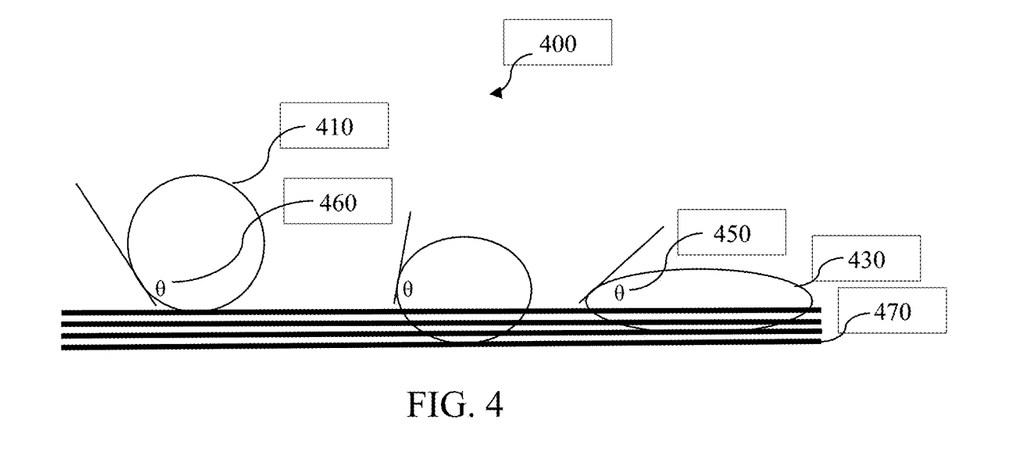
FIG. 4 depicts a block diagram of water droplets on a surface with different wetting properties in accordance with certain embodiments.

In certain embodiments, for a liquid lens to modify its focusing region, either electrowetting or a piezoelectric hydraulic actuator may be applied to a liquid lens. Electrowetting is essentially the phenomenon whereby an electric field may modify the wetting behavior of a droplet, such as water or oil, in contact with an insulated electrode. If an electric field is applied non-uniformly, then a surface energy gradient may be created which may be used to manipulate a droplet sandwiched between two plates. Electrowetting arrays may allow large numbers of droplets to be independently manipulated under direct electrical control without the use of pumps, valves, fixed channels or any moving parts. Electrowetting may involve modifying the surface tension of liquids on a solid surface by using a voltage or current source. By applying a voltage, the wetting properties of a hydrophobic surface may be modified and the surface may become increasingly hydrophilic (wettable). The hydrophobic effect may be the observed tendency of nonpolar substances to aggregate in aqueous solution and exclude water molecules. A hydrophobic surface or effect may explain the separation of a mixture of oil and water into its two components and may explain the beading of water on nonpolar surfaces such as when water beads on a waxed car. A surface that becomes increasingly hydrophilic may improve the ability of a liquid to maintain contact with a solid surface, resulting from intermolecular interactions when the two are brought together. Hydrophobic and hydrophilic are opposites. FIG. 4 illustrates these differences with a fluid droplet on a surface. The fluid droplet 410 on a surface 470 shows very little wetting to the surface, it may be said to be hydrophobic, whereas the droplet 430 shows a fluid on a surface 470 with more wetting to the surface and may be said to be hydrophilic. The more hydrophilic the interaction is said to be, the more that the liquid 430 maintains a large contact area with the solid surface 470 as shown in FIG. 4. Whereas the more hydrophobic the interaction is said to be, the more that the liquid 410 maintains a small contact area with the solid surface 470 as shown in FIG. 4.

Figure 5:
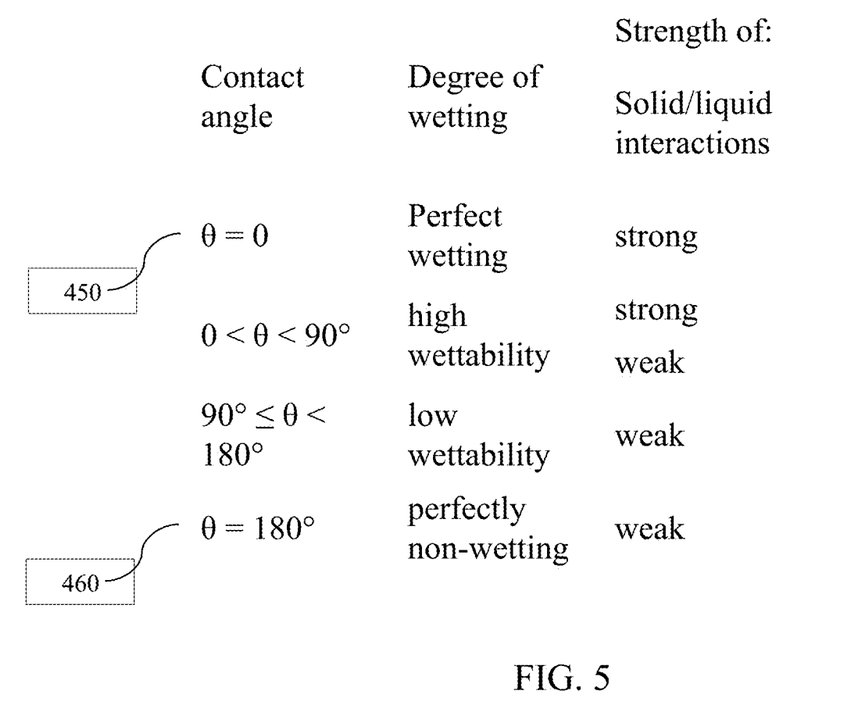
FIG. 5 depicts a table showing the measurement of the degree of wetting along with the strength of solid and liquid interactions in accordance with certain embodiments.

FIG. 5 shows a table that shows how hydrophobic and hydrophilic properties may be measured to determine accurately to what degree a substance may be either hydrophobic or hydrophilic. A contact angle 450 that may be small is said to have more wetting, hydrophilic, and a strong interaction between a solid and a liquid. A contact angle 460 that may be large, for example greater than 180 degrees may be said to be perfectly non-wetting, or in other words very hydrophobic, and may represent a weak interaction between a solid and a liquid.

Figure 6:
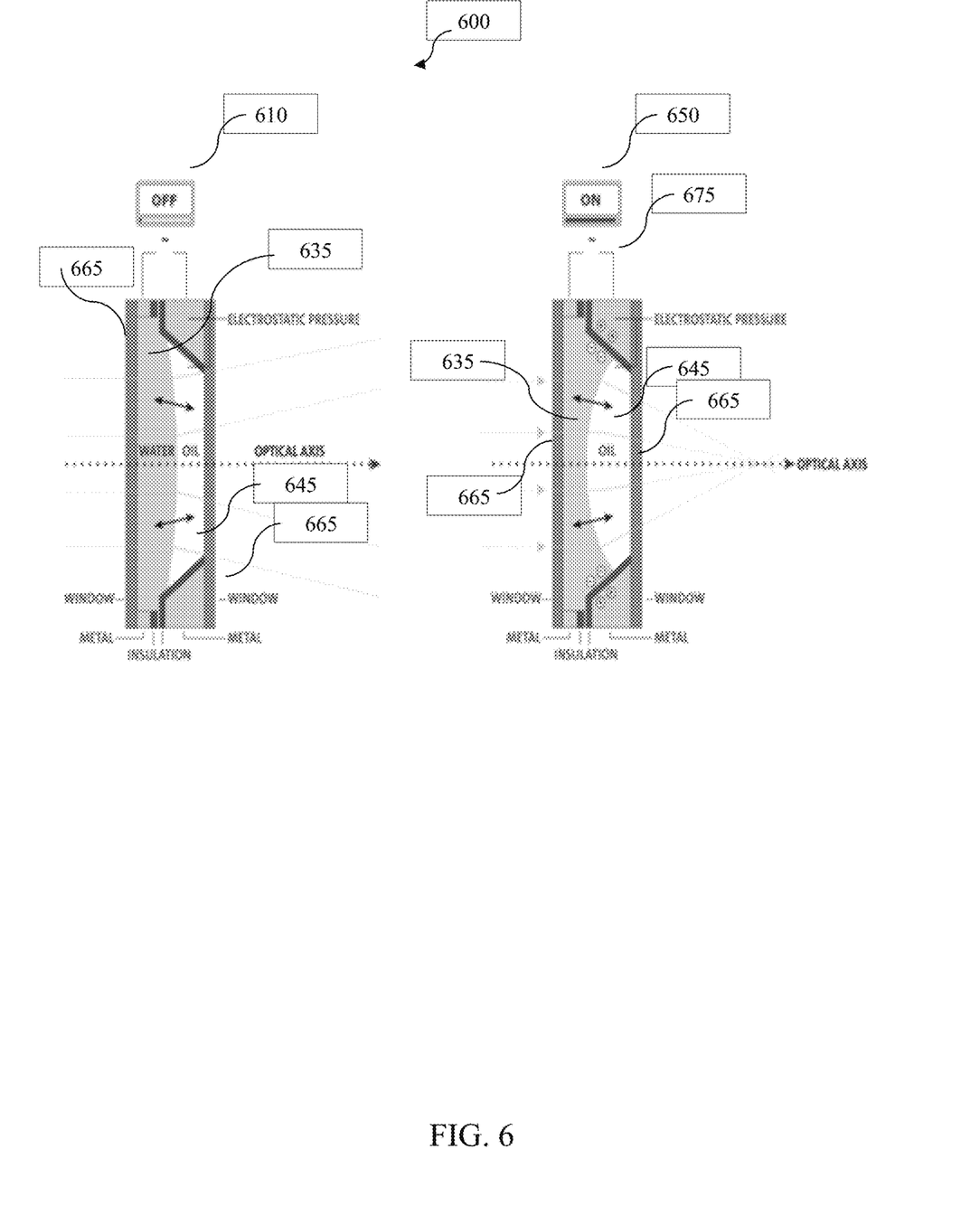
FIG. 6 depicts side views of a typical liquid lens system with two different lens states in accordance with certain embodiments.

Certain embodiments of the electrowetting process with a lens are illustrated in FIG. 6. It depicts two liquid lens assemblies 610 and 650. The first lens assembly has a voltage 675 applied to it and the second lens assembly 610 has no voltage applied to it. The first lens assembly 650 that has a voltage 675 applied to it, which may cause a concave lens 110 to be formed with the water 635 inside the first lens assembly, which may allow for focus of objects far away. The second lens assembly 610 that may have no voltage applied, and may form a convex lens 120 with the water 635 inside the second lens assembly, which may allow for focus of objects nearby. There are more than two focus states that a liquid lens may have depending on the voltage that may be applied to the liquid lens assemblies. There may also be any combination of one or more multiple focus states supported by a liquid lens system 600 by applying different voltage levels to the liquid lens assemblies. Therefore it is understood that the invention is not to be limited to the specific embodiments disclosed, and that modifications and embodiments are intended to be included as readily appreciated by those skilled in the art.

The water 635 inside of the first 610 and second 650 encapsulated liquid lens assemblies may change from being convex 120 for the first lens assembly to concave 110 as a voltage is applied to the first lens assembly. Liquid lenses my use two immiscible fluids, each with a different refractive index, to create variable-focus lenses of high optical quality. In certain embodiments, the two fluids, the first, an electrically conducting aqueous solution 635, and the second, a non-conducting oil 645, may be contained in a short tube with transparent end caps 665. The interior of the tube and one of the caps may be coated with a hydrophobic material, which causes the aqueous solution to form a hemispherical lens-shaped mass (convex or concave) at the opposite end of the tube. The shape of the lens may be adjusted by applying a DC or AC voltage 675 across the coating to decrease its water repellency in a process called electrowetting. In certain embodiments, electrowetting may adjust the liquid's surface tension, changing the radius of curvature in the meniscus and thereby changing the focal length of the lens. A liquid lens may be shock and vibration resistant and such a lens may be capable of seamless transition from convex (convergent) to concave (divergent) lens shapes. In addition, the boundary between the two fluids may form an extremely smooth and regular surface, making liquid lenses of a quality suitable for many applications. The liquid lens may also be controlled by using an AC voltage instead of a DC voltage. Therefore it is understood that the invention is not to be limited to the specific embodiments disclosed, and that modifications and embodiments are intended to be included as readily appreciated by those skilled in the art.

In certain embodiments, a liquid lens may use one or more fluids to create an infinitely-variable lens without any moving parts by controlling the meniscus (the surface of the liquid). In a liquid lens, the internal liquids may change shape and there may also be no moving parts.

In certain embodiments, a piezoelectric hydraulic actuator may also be used to modify the focusing region of the liquid lens. Instead of applying voltage to the liquid lens as with electrowetting, the piezoelectric hydraulic actuator may move the liquid by pumping water in and out through an expanding and contracting membrane. A piezoelectric hydraulic actuator may introduce motion to the liquid of the liquid lens when electricity is applied to the piezoelectric hydraulic actuator.

Figure 7:
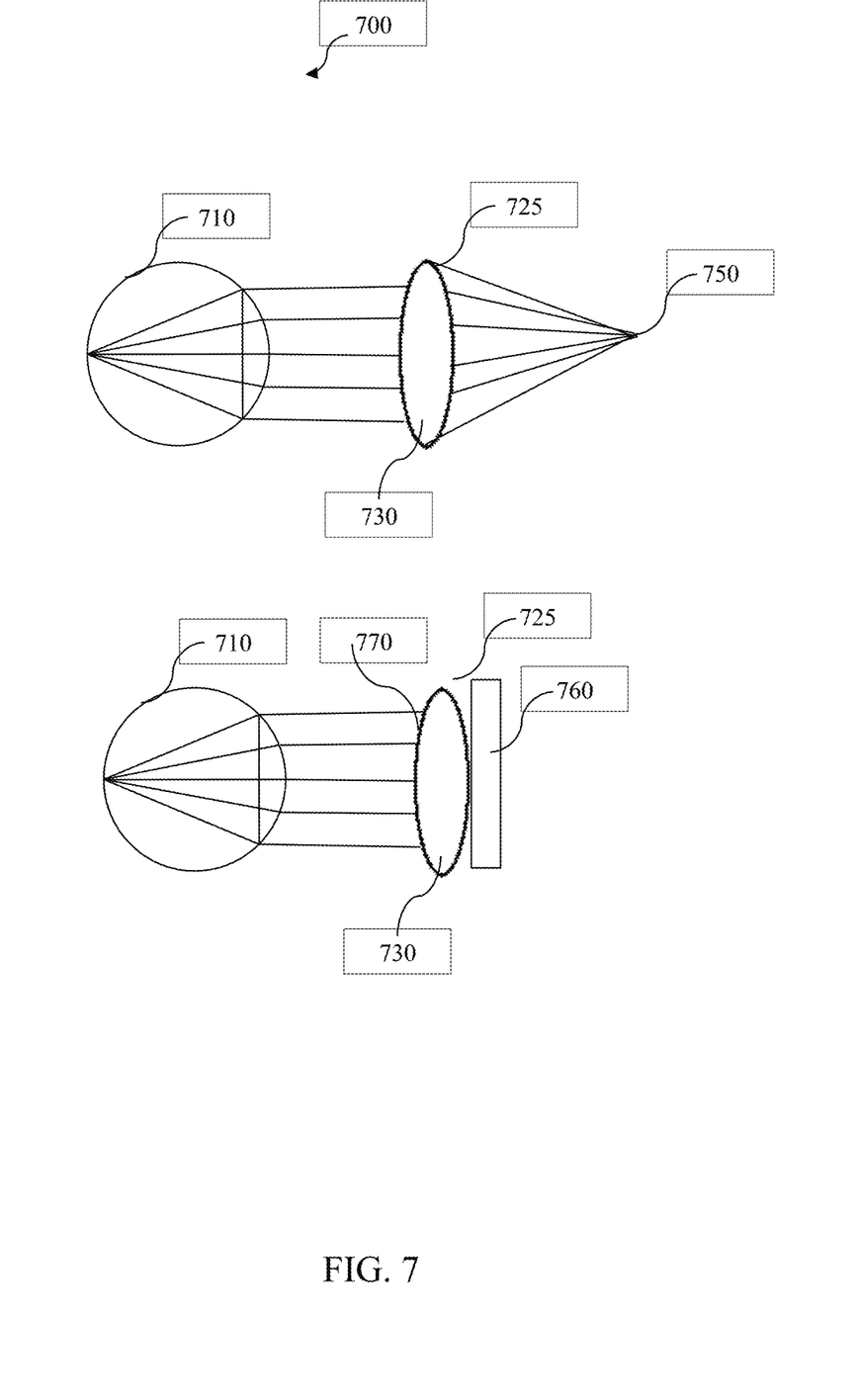
FIG. 7 depicts addition of an occluding device on the outward facing side of a lens in accordance with certain embodiments.

In another embodiment, FIG. 7 depicts adding an occluding device 760 at the outward facing surface 725 of the display lens 730. The outward facing surface of the display lens 725 may be the furthest from the eye 710. An occluding device 760 may block the eye's view of the outside world while the eye may be focusing on the near object 770 on the display lens. When the occluding device 760 is removed from the outward facing surface of the display lens 725, the eye may focus on the far objects 750.

In certain embodiments, the liquid lens system 600 may be modulated or multiplexed at a certain rate to allow cycling back and forth between near and far focus states so that both the near and far objects appear to be in focus simultaneously through the use of persistence of vision. Persistence of vision is the phenomenon of the eye by which an afterimage is thought to persist for approximately one twenty-fifth of a second on the retina. An afterimage, ghost image or image burn-in may be an optical illusion that refers to an image continuing to appear in one's vision after the exposure to the original image has ceased. One of the most common afterimages is the bright glow that may seem to float before one's eyes after looking into a light source for a few seconds. In certain embodiments, by multiplexing the liquid lens system 600, the eyes may appear to be in focus on both the near and far objects simultaneously by taking advantage of the persistence of vision phenomenon.

Figure 8:
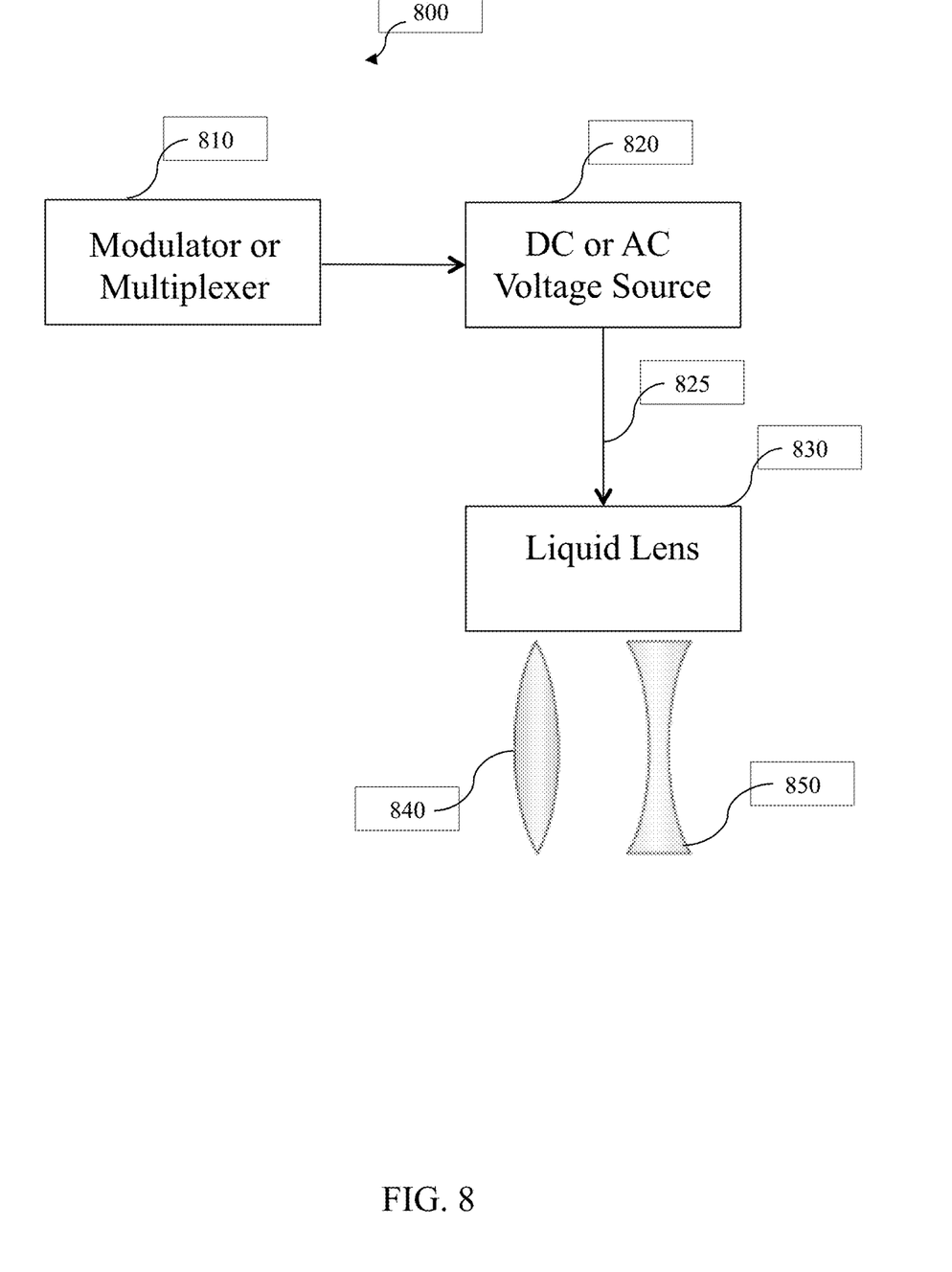
FIG. 8 depicts a liquid lens system that may be multiplexed in accordance with certain embodiments.

In certain embodiments, the liquid lens system 800 may comprise a multiplexer or a modulator 810, which modulates a DC or AC voltage source 820. The modulated output of the source 825 may be connected to the liquid lens 830. The modulated source may cause the liquid lens to change its lens shape from convex 840 to concave 850. The modulated source, for example, may also change the focus state from a far focus state to a more far focus state. The modulated source, for example, may also change the focus state from a near focus state to a more near focus state. There are many focus states that a liquid lens may perform depending on the voltage of the DC or AC voltage source 820. The lens may, for instance, focus on an object using one convex lens and then focus on an object further away with a different convex lens. There may also be any combination of one or more multiple focus states supported by a liquid lens system 800 such as three focus states, four focus states, five focus states, etc. to an infinite number of focus states. Therefore it is understood that the invention is not to be limited to the specific embodiments disclosed, and that modifications and embodiments are intended to be included as readily appreciated by those skilled in the art. The liquid lens 830 may typically change from convex 840 to concave 850 at a rate of approximately 1 ms to allow both the near and far-away images to be in focus simultaneously.

Figure 9:
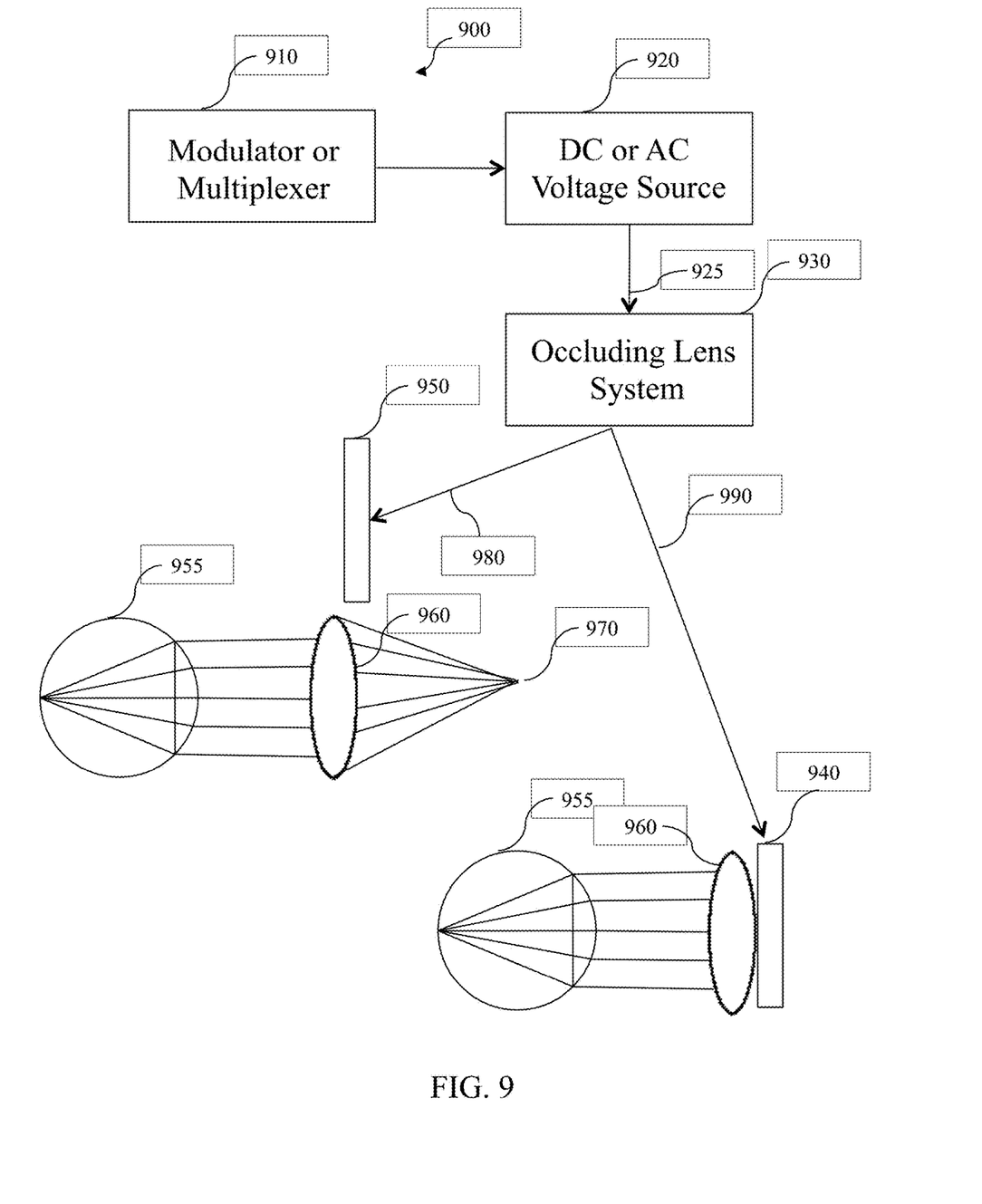
FIG. 9 depicts a lens system with an occluding device that may be multiplexed in accordance with certain embodiments.

In certain embodiments as shown in FIG. 9, the occluding lens system 900 may comprise of a multiplexer or a modulator 910, which modulates a DC or AC voltage source 920. The modulator may also modulate DC or AC current to control the occluding lens system. It is understood that the invention is not to be limited to the specific embodiments disclosed, and that modifications and embodiments are intended to be included as readily appreciated by those skilled in the art. The modulated output of the voltage source 925 may be connected to an occluding lens system 930. The modulated voltage 925 may cause the occluding object 950 and 940 to transition from the blocking state 990 to the non-blocking state 980. In the blocking state 990, the occluding object 940 may block the eye 955 on the outward facing (furthest from the eye) surface of the display lens 960. This may allow the eye 955 to view the information on the display lens and not view the surroundings. In the non-blocking state 980, the occluding object 950 does not block the eye 955 from viewing through the lens to objects that are beyond the display or the lens 960. An occluding device 940 may block the eye's view of the outside world while the eye focuses on the near objects on the display or the lens. When the occluding device 950 is removed from the outward facing surface of the display lens 960, the eye may focus on the far objects 970.

In certain embodiments, the occluding object may be modulated at a rate that is approximately 1 ms to allow both the near and far-away images to simultaneously be in focus due to the persistence of vision. Therefore, it is understood that the invention is not to be limited to the specific embodiments disclosed, and that modifications and embodiments are intended to be included as readily appreciated by those skilled in the art.

Figure 10:
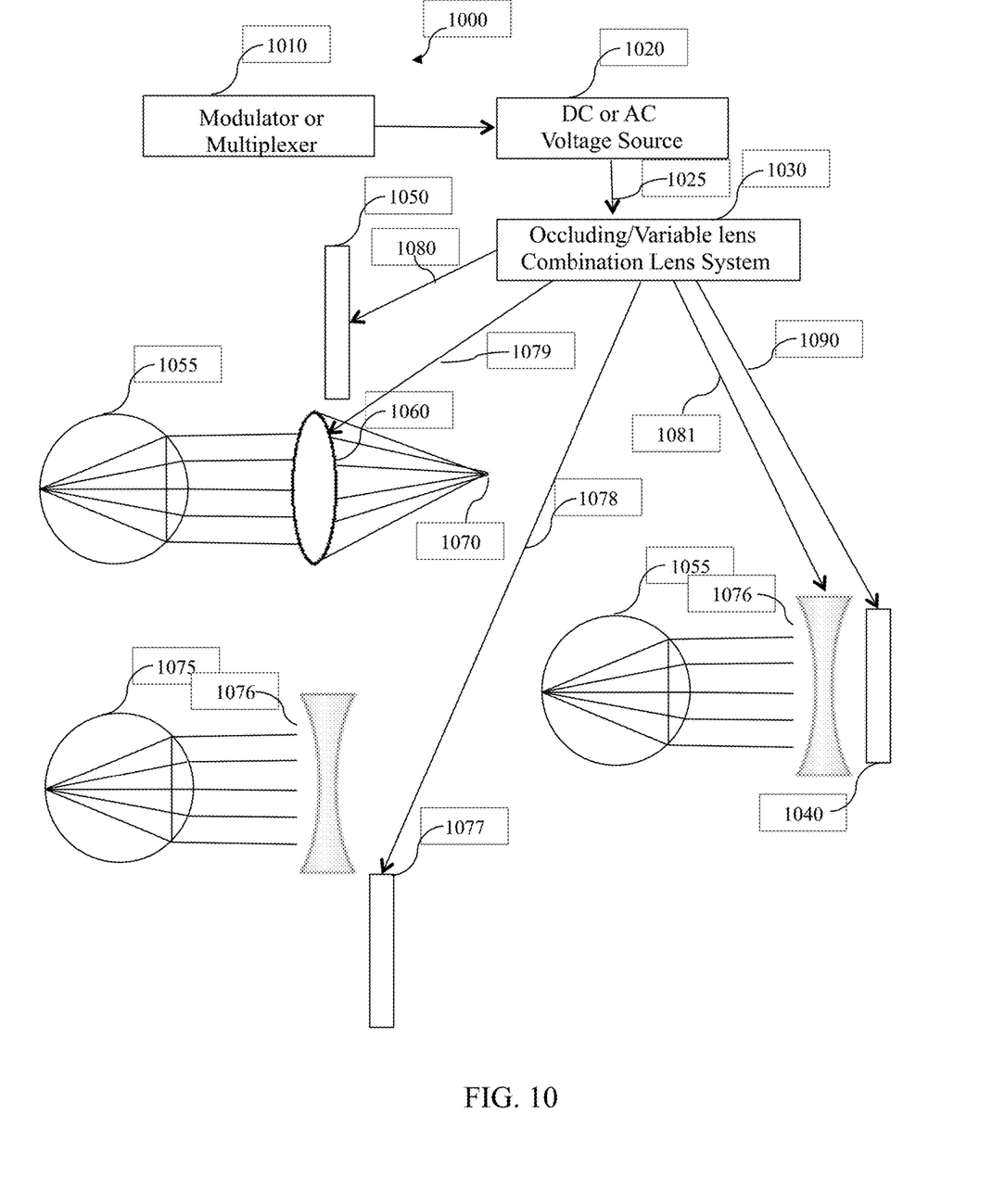
FIG. 10 depicts a liquid lens system that may be multiplexed in combination with an occluding device in accordance with certain embodiments.

In certain embodiments, the occluding lens system and a variable focus lens such as a liquid lens may be used together with multiplexing. The occluding/variable lens combination lens system 1000 may comprise a multiplexer or a modulator 1010, which modulates a DC or AC voltage source 1020. The modulator may also modulate DC or AC current to control the occluding/variable lens combination lens system. It is understood that the invention is not to be limited to the specific embodiments disclosed, and that modifications and embodiments are intended to be included as readily appreciated by those skilled in the art. The modulated output of the voltage source 1025 may be connected to an occluding/variable lens combination lens system 1030. The modulated voltage 1025 may cause the occluding device 1050 and 1040 to move from the blocking state 1090 to the non-blocking state 1080. In the blocking state 1090, the occluding object 1040 may block the eye 1055 on the outward facing (furthest from the eye) surface of the display lens 1060. This allows the eye 1055 to view the information on the display lens and not view the surroundings. While the occluding device is in the blocking state 1090 the variable focus lens, such as a liquid lens may change states, for example, from a convex lens 1060 to concave lens 1076. When the liquid lens state has completed its variation from one lens state to another, the occluding device 1077 may be removed so that the eye 1075 may see through the new focal length lens 1076. This new focal length lens 1076 may be either a convex or a concave lens at any focal length.

In certain embodiments, in the non-blocking state 1078, the occluding object 1077 does not block the eye 1075 from viewing through the lens to objects that are at the display lens 1076 or beyond the display lens 1076. An occluding device 1040 may block the eye's view of the outside world while the eye focuses on the near objects on the display lens. When the occluding device 1077 is removed from the outward facing surface of the display lens 1076, the eye may focus on objects at a new focal length.

In certain embodiments, the occluding object and the variable focus lens may be modulated at a rate that is approximately 1 ms to allow both the near and far-away images to simultaneously be in focus due to the persistence of vision. Therefore, it is understood that the invention is not to be limited to the specific embodiments disclosed, and that modifications and embodiments are intended to be included as readily appreciated by those skilled in the art.

While the above description contains many specifics and certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art, as mentioned above. The invention includes any combination or subcombinations of the elements from the different species and/or embodiments disclosed herein.

The various embodiments described above can be combined to provide further embodiments. All of the commonly assigned US patent applications, foreign patents, foreign patent applications and non-patent publications referred to in this specification and/or listed in the Application Data Sheet, including but not limited to U.S. patent application Ser. No. 13/669,668 filed on Nov. 6, 2012 are incorporated herein by reference, in their entirety.

The invention claimed is:

1. A lens system, comprising:
   a variable focus lens; and
   a modulation device operatively coupled to the variable focus lens to selectively vary the focus of the variable focus lens, in operation, the modulation device alternatingly switches the focus of the variable focus lens between a near-focus state and a far-focus state at a switching rate that allows both near images and far-away images viewed by a user through the same point in the variable focus lens to appear in focus simultaneously due to the user's persistence of vision.

2. The lens system of claim 1 wherein the lens system is a lens system of a head-mounted display device.

3. The lens system of claim 1 wherein the modulation device alternatingly switches the focus of the variable focus lens with a switching time of 1 millisecond.

4. The lens system of claim 1 wherein the modulation device alternatingly switches the focus of the variable focus lens with a switching time of 1 millisecond and a steady-state time of 8 milliseconds between switches.

5. The lens system of claim 1 wherein the modulation device changes the variable focus lens from a convex lens to a concave lens.

6. The lens system of claim 1 wherein the variable focus lens changes the lens from a first convex lens to a second convex lens.

7. The lens system of claim 1 wherein the variable focus lens changes the lens from a first concave lens to a second concave lens.

8. The lens system of claim 1 wherein the variable focus lens changes the lens from a concave lens to a convex lens.

9. The lens system of claim 1, further comprising:
   a voltage supply connected to the variable focus lens wherein the modulation device varies the focus of the variable focus lens by varying the voltage supplied to the variable focus lens.

10. The lens system of claim 1, further comprising:
    a current supply connected to the variable focus lens, wherein the modulation device varies the focus of the variable focus lens by varying the current supplied to the variable focus lens.

11. The lens system of claim 1, further comprising:
    a piezoelectric hydraulic actuator operatively coupled to the variable focus lens and the modulation device, the piezoelectric hydraulic actuator operative to vary the focus of the variable focus lens in response to an input from the modulation device.

12. The lens system of claim 1 wherein the modulation device is a multiplexer.

13. The lens system of claim 1, further comprising:
    an electro wetting device operatively coupled to the variable focus lens and the modulation device, the electro wetting device operative to vary the focus of the variable focus lens in response to an input from the modulation device.

14. The lens system of claim 1 wherein the variable focus lens comprises a liquid variable focus lens, a switchable diffractive grating, or an electroactive polymer.

15. The lens system of claim 1, further comprising:
    an occluding element configured to selectively block at least a portion of the field of view of the variable focus lens to prevent viewing of far-away images through the variable focus lens.

16. The lens system of claim 15 wherein the occluding element is configured to selectively block at least a portion of the field of view of the variable focus lens while the focus state of the variable focus lens is being changed.

* * * * *